United States Patent
Krishna et al.

(10) Patent No.: US 9,475,028 B2
(45) Date of Patent: *Oct. 25, 2016

(54) SYSTEMS AND METHODS BASED ON RADIATION INDUCED HEATING OR IGNITION OF FUNCTIONALIZED FULLERENES

(75) Inventors: Vijay Krishna, Gainesville, FL (US); Brij Moudgil, Gainesville, FL (US); Ben Koopman, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 1610 days.

This patent is subject to a terminal disclaimer.

(21) Appl. No.: 12/479,300

(22) Filed: Jun. 5, 2009

(65) Prior Publication Data
US 2009/0302029 A1 Dec. 10, 2009

Related U.S. Application Data

(63) Continuation-in-part of application No. PCT/US2007/084956, filed on Nov. 16, 2007.

(60) Provisional application No. 60/868,633, filed on Dec. 5, 2006.

(51) Int. Cl.
*B23K 26/04* (2014.01)
*B01J 19/12* (2006.01)
(Continued)

(52) U.S. Cl.
CPC ............ *B01J 19/123* (2013.01); *A61N 5/00* (2013.01); *B01J 19/121* (2013.01); *B01J 19/125* (2013.01); *B01J 19/126* (2013.01); *B01J 19/127* (2013.01); *B01J 19/128* (2013.01); *B01J 19/129* (2013.01);
(Continued)

(58) Field of Classification Search
CPC . A61B 18/1815; A61B 18/18; B23K 26/032
USPC .............. 219/678, 121.61, 121.6, 121.62
See application file for complete search history.

(56) References Cited

U.S. PATENT DOCUMENTS 5,627,353 A * 5/1997 Oeste .................. 204/157.15
5,739,376 A   4/1998 Bingel
(Continued)

FOREIGN PATENT DOCUMENTS

DE   4339053   6/1994
EP   1939140   7/2008
(Continued)

OTHER PUBLICATIONS

Ajayan, P.M., et al., "Nanotubes in a Flash-Ignition and Reconstruction", *Science*, Apr. 26, 2002, p. 705, vol. 296.
(Continued)

*Primary Examiner* — Dana Ross
*Assistant Examiner* — Ayub Maye
(74) *Attorney, Agent, or Firm* — Saliwanchik, Lloyd & Eisenschenk

(57) ABSTRACT

A method of irradiating a target region containing at least one fullerene comprising molecule promotes the heating or combustion of the target region. The heating method can be employed in a variety of applications including: selective targeting and destruction of cancer cells, detonation of explosives, ignition of a combustible mixture, photolithographic processes, and writing of optical storage media.

14 Claims, 4 Drawing Sheets

(a)

(b)

(51) Int. Cl.
    *A61N 5/00*    (2006.01)
    *C06B 23/00*   (2006.01)
    *C06C 9/00*    (2006.01)
    *A61N 5/06*    (2006.01)
    *A61N 5/10*    (2006.01)

(52) U.S. Cl.
    CPC ............... *C06B 23/001* (2013.01); *C06C 9/00* (2013.01); *A61N 5/062* (2013.01); *A61N 5/10* (2013.01)

(56) References Cited

U.S. PATENT DOCUMENTS

| | | | |
|---|---|---|---|
| 5,994,410 A | 11/1999 | Chiang et al. | |
| 6,162,926 A | 12/2000 | Murphy et al. | |
| 7,208,191 B2* | 4/2007 | Freedman | B82Y 30/00 257/E23.11 |
| 2001/0051766 A1* | 12/2001 | Gazdzinski | 600/309 |
| 2003/0118657 A1* | 6/2003 | West et al. | 424/489 |
| 2003/0129436 A1* | 7/2003 | Ramm et al. | 428/519 |
| 2003/0156991 A1* | 8/2003 | Halas et al. | 422/100 |
| 2006/0162828 A1* | 7/2006 | Koch | 149/19.8 |
| 2006/0181854 A1* | 8/2006 | Freedman | B82Y 30/00 361/705 |
| 2007/0062411 A1* | 3/2007 | Weisman et al. | 106/31.15 |

FOREIGN PATENT DOCUMENTS

| | | |
|---|---|---|
| JP | 2005-538033 | 12/2005 |
| WO | WO 02 24273 | 3/2002 |
| WO | WO 03-047633 | 6/2003 |
| WO | WO 2006 113785 | 10/2006 |
| WO | WO 2008 082724 | 7/2008 |

OTHER PUBLICATIONS

Tsuji, M., et al., "Formation of hydrogen-capped polyynes of laser ablation of $C_{60}$ particles suspended in solution," *Carbon*, Jan. 1, 2003, pp. 2141-2148, vol. 41, No. 11.

Diederich, F. et al., "The Higher Fullerenes: Isolation and Characterization of $C_{76}$, $C_{84}$, $C_{90}$, $C_{94}$, and $C_{70}O$, an Oxide of $D_{5h}$-$C_{70}$", *Science*, Apr. 26, 1991, pp. 548-551, vol. 252, No. 5005.

Smart, C. et al., "Extraction of giant fullerenes molecules, and their subsequent solvation in low boiling point solvents," *Chemical Physics Letters*, Jan. 10, 1992, pp. 171-176, vol. 188, No. 3,4.

* cited by examiner

*Fig. 4*

SYSTEMS AND METHODS BASED ON RADIATION INDUCED HEATING OR IGNITION OF FUNCTIONALIZED FULLERENES

CROSS-REFERENCE TO RELATED APPLICATIONS

This application is a continuation-in-part of International Patent Application No. PCT/US2007/084956, filed Nov. 16, 2007, which claims the benefit of U.S. Provisional Patent Application Ser. No. 60/868,633, filed Dec. 5, 2006, the disclosures of which are hereby incorporated by reference in their entirety.

The subject invention was made with government support under a research project supported by National Science Foundation, Contract No. EEC9402989. The government has certain rights to this invention.

FIELD OF THE INVENTION

The invention relates to systems and methods based on the radiation induced heating or ignition of carbon nanomaterials, more particularly to heating or ignition of functionalized fullerenes.

BACKGROUND

Many current industrial processes that utilize a fuel or an oxidation reaction often require an initiation stimulus, or an ignition source, to start the reaction to release energy (e.g., heat, light). A device which achieves this goal is a critical system component for most combustion processes. Although many different ignition methods exist, the most popular is the electric spark igniter. However, spark igniters require high-energy input supplied by a high-voltage circuitry and by its nature is a single-point stimulus method. Other ignition methods, such as plasma jet injection or flame jet initiation and high-power laser ignition, are all bulky, heavy, and expensive to operate.

There have been some recent reports of optical ignition of carbon nanotubes in oxidizing gaseous ambients, such as in air. For example, researchers have reported that single-walled carbon nanotubes ignite when exposed to a conventional photographic flash (Ajayan et al., "Nanotubes in a Flash-Ignition and Reconstruction", Science, Vol. 296, Apr. 26, 2002). This photoeffect is disclosed to occur for single-walled carbon nanotubes prepared by carbon arc, laser ablation, or chemical vapor deposition techniques upon exposure to a camera flash at close range. Ignition and burning are reported to occur when local increases in temperature are sufficient to initiate the oxidation of the carbon and propagate as more heat is released by the exothermic reaction. Heat confinement in nanostructures can thus lead to drastic structural reformation and, under oxidizing environments, induce ignition under conditions not expected for bulk materials. The heat pulse is created by light absorption by the nanotubes from a proximal light flash.

Applications of optical heating or ignition of carbon nanotubes are limited by several characteristics of carbon nanotubes that include size, high aspect ratio, insolubility in water or other liquids, and lack of biocompatibility. Compositions are needed that provide radiation induced heating or ignition in water or other liquids as well as air, have small size and low aspect ratio, and are soluble in water or other liquids. Moreover, preferably such compositions are biocompatible to allow use in medical applications.

SUMMARY OF THE INVENTION

A method of localized heating includes the steps of disposing a plurality of fullerene comprising molecules in at least one target region and irradiating the fullerene comprising molecules with electromagnetic radiation having a wavelength and intensity sufficient to convert the radiation to thermal energy at the fullerene comprising molecules, heating the target regions. The fullerene comprising molecules can be heated to a state of combustion. The fullerene comprising molecules can be endohedral fullerenes, substituted fullerenes, functionalized fullerenes or any mixture of these fullerenes. The target region is within or in contact with a material that can be an organic gas, liquid or solid; an inorganic gas, liquid, or solid; a polymeric or polymer composite; water, an aqueous solution or aqueous suspension; a metal or metal alloy, a glass or ceramic; or a biological or biologically derived material or mixture of these materials. The electromagnetic radiation can be at least one of gamma rays, x-ray, extreme ultraviolet, ultraviolet, visible, infrared, microwave or radio-wave radiations.

The method can be used as a photoresist where the target region is within a resist coating, with the fullerene comprising molecules disposed within or contacting the coating where negative features or voids can be formed in the resist coating by thermally induced decomposition in the target regions of the coating when the heating results from irradiation of the target area. When irradiation results in thermally induced reactions or physical phase transformations in the target regions of the coating, an etchant can be used to remove the target region leaving negative features in a coating or channels within the coating. When the irradiation induces reactions, such as thermal cross-linking, an etchant can be used to remove all but the target regions leaving positive features from the resist coating. Alternately, negative features can be created directly on a photoresist containing fullerene comprising molecules upon irradiation with no need for an additional etching step. Alternately, a solution of fullerene comprising molecules can be used as a photoresist.

The method can be used for welding a plurality of polymer or polymer composite pieces by irradiating the interface of the pieces using a laser beam with the fullerene comprising molecules disposed within or contacting the interface so that the polymer at the interface melts and fuses into the weld upon cooling.

The method can be used for soldering where the heat generated upon irradiation of the fullerene comprising molecules within or contacting the solder melts the solder at the target region. Soldering of surfaces can be carried out remotely in this manner.

The method can be employed for alternate and enhanced methods of writing to writable memory media such as CDs and DVDs. The fullerene comprising molecules can be at or in a layer of an organic dye or a metal alloy to amplify and accelerate the physical or chemical changes of the target regions of the layer that changes optical properties of the layer in the target region to encode information. Such changes can be reversible or irreversible. The layer can be fullerene comprising molecules without the dye or alloy such that decomposition of the fullerene comprising molecules in the target region of the layer results in irreversible or reversible changes in the optical properties of the layer in the target region.

The method can be employed in a device to act in a manner similar to a spark plug where the target region is an end of a tube filled with the fullerene comprising molecules and where the end of the tube is in communication with a combustion chamber. When the combustion chamber contains a fuel-oxidizer mixture, irradiation of the end of the tube by a laser beam can result in ignition of the fullerene comprising molecules and the fuel oxidizer mixture in the chamber. The device can also have a plunger in the tube to move uncombusted fullerene comprising molecules to a position at the end of the tube for a subsequent ignition in the chamber.

The method can also be used where fullerene comprising molecules are dissolved or suspended in a fuel prior to introduction to a combustion chamber such that an irradiation in the chamber results in ignition of the fullerene comprising molecules and the fuel oxidizer mixture. Such a fuel and ignition system would have little or no temperature sensitivity.

The method can be used for detection and destruction of hazardous bioparticulates where fullerene comprising molecules, which contain a portion that is an aptamer or antibody or functionalized fluorescent antibody or dye/quantum dot doped silica particle, are contacted with the bioparticulates. Where a plurality of fullerene comprising molecules conjugate to a bioparticulate, low intensity irradiation promotes fluorescence of the conjugated bioparticulates to locate the target regions and once located a sufficiently intense directed irradiation of the located targets can ignite the fullerene comprising molecule and destroy the bioparticle.

The method can be used to target cancer cells within a patient. The fullerene comprising molecules can be directed to the target region of cancer cells and upon irradiation of the target region cause the cancer cells to undergo apoptosis or necrosis, or to burst or to suffer other consequences of heating or ignition so that their growth is inhibited. One method of directing the fullerene comprising molecules to the cancer cells is to have a targeting group as part of the fullerene comprising molecule where the targeting group associates the fullerene comprising molecule with the cancer cells. Radiation can be used to activate the fullerene comprising molecules thermally to destroy the target without promoting damage to non-targeted regions of tissue.

The method can be used for initiation of an explosion. The fullerene comprising molecules in direct or indirect contact with an explosive material can be combusted by irradiation to detonate explosive materials.

The method can be employed as a micro or nano-thruster where the target region contains fullerene comprising molecules and optionally another propellant, such that upon irradiation of the target region they combust to generate gases that provide a thrust.

The method can be used for solar heating application where the fullerene comprising molecules decorate the surface of a metal. Solar irradiation of the decorated surface causes heat to be transferred to the metal and ultimately to water or another medium on the opposite side of the metal.

A system for heating a target region includes at least one fullerene comprising molecule disposed in the target region with an irradiation source that can direct radiant energy to the target region as desired. The irradiation can be from any source, such as a laser, a lamp, or sunlight. The period of irradiation can be controlled by a switch activated either manually or automatically controlled by a computer or other device, by opening and closing a shutter situated between a source of radiant energy and the target region, again activated either manually or automatically.

BRIEF DESCRIPTION OF THE DRAWINGS

A fuller understanding of the present invention and the features and benefits thereof will be obtained upon review of the following detailed description together with the accompanying drawings, in which:

FIG. 3(a)-(d) shows images before, 1 second after, 10 seconds after, and nearby cells 10 seconds after radiation induced ignition of PHF coated folate conjugated silica nanoparticles in A549 cells.

DETAILED DESCRIPTION OF THE INVENTION

A method of remotely activated localized heating comprises the steps of disposing a plurality of fullerene comprising molecules in a target region. The fullerene comprising molecules are irradiated with electromagnetic radiation having a wavelength and intensity sufficient to heat, and in some embodiments heating is accompanied by combustion of the fullerene comprising molecules. The fullerene comprising molecules absorb radiant energy and convert the radiant energy into thermal energy to supply heat to the target region.

The present invention is based on the unexpected finding that fullerene comprising molecules, upon irradiation using a suitable source, heat, ignite or combust without the need for a spark, flame or other conventional initiator to produce significant local heating. Heating or ignition can occur in a gaseous, liquid, or solid environment. In air, the ignition leads to rapid decomposition. A bright flash of visible light can be observed before combustion. The heating can be nearly undetectable as a temperature increase in some environments. As is readily understood by those skilled in the art, a photo-induced thermal effect need not dissipate the thermal energy as a temperature increase, but can also be dissipated as a different thermodynamic parameter, such as a pressure change. In some environments, the irradiation of the fullerene comprising molecules can generate heat that causes expansion of the fullerene which then dissipates a significant portion of the energy as a pressure wave, a photoacoustic effect, rather than by a significant temperature increase. The resulting heat induced change to the target region can be due to a photoacoustic shockwave exclusively or in combination with a temperature increase, particularly in some embodiments of the invention where biological cells are disrupted. Stated otherwise, the thermal energy caused by photon absorption generates vibrational or other induced intra- or extra-molecular motion, which generates heat and pressure changes that affect the target region.

Although the visible and near infrared (NIR) radiation has been demonstrated to provide significant heating including ignition according to embodiments of the present invention, other wavelength ranges could provide significant heating or ignition. For example, IR radiation generally, as well as UV, microwave and radio-wave radiation can be useful for producing significant heating or for inducing ignition.

Fullerenes are generally in the form of a spheroidal carbon comprising structure and are thus distinct from carbon nanotubes, which are essentially tubes with graphene surfaces. In contrast to the surface of carbon nanotubes, fullerenes have both five carbon and six carbon ring structures. Carbon nanotubes and fullerenes are physically and chemically stable molecules. Unlike carbon nanotubes and fullerenes, some functionalized fullerenes are known to be biocompatible and can have therapeutic properties.

The term "fullerenes" defines a general class of molecules that exists essentially in the shape of a three dimensional polyhedron containing from 20 to 1500 carbon atoms, and which comprises carbon atoms as the predominant atomic moiety from which they are composed. The fullerene comprising molecules include but are not limited to fullerenes such as C-28, C-32, C-44, C-50, C-58, C-60, C-70, C-84, C-94, C-250 and C-540. (According to this nomenclature, the fullerene which contains 60 carbon atoms is denoted C-60, the fullerene which contains 70 carbon atoms is denoted C-70, etc.) Also included among the fullerene comprising molecules for purposes of the invention are the substituted fullerenes. These are molecular fullerenes which have had one or more of the atoms which comprise the fullerene cage structure replaced by an atom other than carbon, yet essentially retain the geometry of a polyhedron upon being so substituted. Also included among the fullerene comprising molecules for the purpose of the invention are endohedral fullerenes, in which atoms of elements other than carbon (e.g., iron) reside inside the cage structure of fullerenes. The fullerene comprising molecules for the purpose of the invention also include functionalized fullerenes, in which different functional groups are bonded to the fullerene cage via covalent bonds, or ionic bonds, or Dewar bonds, or Kubas interactions, or mixtures of these bonds. Functionalized fullerenes refer to fullerenes ($C_x$ where x is 20 to 1500) with side groups attached to the cage. The side groups can be either inorganic, including but not exclusive to —OH, —Br, —H, —Ti, or organic, including but not exclusive to —C(COOH)$_2$ or combinations of organic and/or inorganic. The number of side groups attached per cage of fullerene can vary from 1 to a majority of the number of carbons in the fullerene cage. Functionalized fullerenes have different physical and chemical properties based on the type and number of side groups. The fullerene comprising molecules have dimensions that can be in excess of a nanometer in diameter, and can be considered nanoparticles.

In one embodiment of the invention, functionalized fullerenes do not have nitrogen in their structure, and have no measurable metal impurities associated with them. Two exemplary, but non-limiting, functionalized fullerenes are described in some detail below. Both of these fullerenes are generally commercially available.

Figure 1:
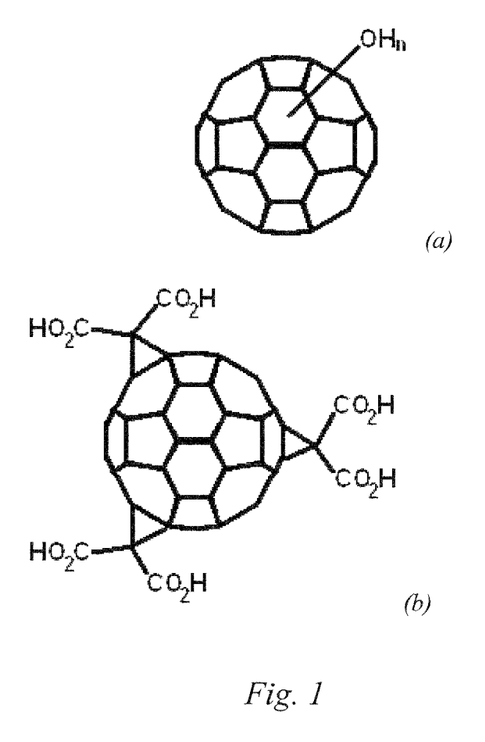
FIG. 1 shows the structure of exemplary functional fullerenes of various embodiments of the invention (a) $C_{60}(OH)_n$ (n~1-48) and (b) $C_{63}(COOH)_6$.

Polyhydroxyl fullerene derivatives (PHF), for example formula $C_{60}(OH)_n$ (n~1-48) shown in FIG. 1(a) were first reported by Chiang, L. et. al. (*J. Chem Soc, Chem. Commun.* 1992, 1791). PHF, also referred to as fullerols or fullerenols, are useful for the formation of gels, starburst polymers, and composites and may be used as therapeutics. The number of —OH groups is typically between 1 and 48. Polyhydroxy fullerene derivatives can be further derivatized to form other functionalized fullerenes according to embodiments of the invention. For example, the OH can be converted into ethers or esters to yield functionalized fullerenes with enhanced miscibility with aqueous or non-aqueous environments.

Carboxy fullerenes, for example formula $C_{63}(COOH)_6$ shown in FIG. 1(b), are water soluble and are reported to have therapeutic properties by Dugan et al. (*Proc. Natl. Acad. Sci.,* 1997 Vol 94, 9434-9439). Again such carboxy fullerenes can be farther derivatized, for example by esterification or amidation reactions, to form other functionalized fullerenes for use in various embodiments of the invention.

Other exemplary functionalized fullerenes include N-ethyl-polyamino-C60, [6, 6] phenyl C60 butyric acid methyl ester (PCBM), fullerene hydride and N-methyl fulleropyrrolidine. Certain polymer chains can also be used as functional groups.

Highly localized heating provided by the method of the invention can be used for a wide variety of useful applications. For example, in one embodiment of the invention fullerene comprising molecules can be used for photolithography. The water-soluble nature of some functionalized fullerenes, such as PHF, can be used to coat a variety of substrates and can be removed using water upon completion of an etching step of a photolithography process. Alternately, functionalized fullerenes soluble in a different solvent suitable for photolithography can also be used. Current nanolithography is usually carried out by e-beam lithography (commercial scale), focused ion-beam and dip-pen lithography. The latter two are not performed commercially since the processes are quite time consuming. E-beam lithography depends on the energy of electron beam breaking the polymer chains of the resist film.

Functionalized fullerenes, such as PHF, can be used as a component in a coating system on a resist according to an embodiment of the invention where the process can operate at atmospheric pressure and be cost-effective because radiation such as x-ray, UV, visible, NIR, and microwave over a range of wavelengths can be absorbed by the fullerene particles. Functionalized fullerenes can be included in the coating system above or below the resist or mixed with the resist as long as the laser or other radiation source can be focused on them. The minimum width achieved by e-beam nanolithography is now about 20 nm. The etching as a result of heat generated by localization in functionalized fullerene molecules can be controlled by the spot size of the irradiation. In principle, the line width achieved through etching according to the invention can be as small as 1.0 nm, which is the cross-section of a functionalized C-60 molecule. Fullerenes of lower carbon number have smaller cross-sections. Ignition or heating of the fullerenes to a degree where the coating undergoes thermal degradation can form negative features in the coating. Heating provided by fullerenes according to the invention which is short of ignition can induce other changes in the coating system. For example, this phenomenon can be applied in nanolithography for assisting in a chemical etching, for example a caustic etching of a polymer resist or a physical etching, for example a heat and/or vacuum promoted volatilization of a polymer resist, where the change can either act as a positive resist where only the irradiated features remain after etching or a negative resist where only the irradiated features are removed by etching. A coating of functionalized fullerenes applied directly to a wafer or MEMS/NEMS substrate can also be used as a resist for nanolithography; for example, a solution of PHF in water with viscosity enhancers can be coated as a resist.

In one embodiment, the inventive coating can be used to create nano or microfluidic devices or to create nanoscale patterns by nanolithography. Functionalized fullerenes comprising coatings, such as PHF coatings, can be applied in other processes involving pattern forming, etching or cutting.

Functionalized fullerenes according to an embodiment of the invention such as PHF can also be used for polymer welding. The welding method can include functionalized fullerenes included in a polymer composite or adhering to an edge of a polymer. When two or more pieces with functional fullerenes situated within or at the interface of two contacting surfaces are irradiated, local melting occurs at the interface in the region about the functionalized fullerenes. For example the interface between two polymer pieces with functionalized fullerenes can be irradiated selectively by a laser at an intensity that causes heating without ignition of the functionalized fullerenes to melt the polymer at the interface with the formation of the weld upon cooling.

In another embodiment of the invention the optical heating or ignition properties of functionalized fullerenes can be used for localized soldering on various substrates. One example of an application of soldering with functionalized fullerenes is micro-hole repairs in vessels. Functionalized fullerenes can be included in a thin tape, or other patch structure, such that an alloy with a low melting point can be applied to an area for repair. Laser irradiation of the tape can induce localized melting of the tape such that the molten tape can seal micro-holes. In this embodiment the functionalized fullerenes can be mixed with a soldering alloy and laser irradiation of the functionalized fullerenes can generate heat for soldering. The method provides an alternative to electrical heating for soldering. An advantage of using a radiation source to melt solder instead of electrical heating is evident for under-water soldering applications. Such soldering can be carried out remotely using a laser such that no human presence at the point of soldering is required. Remote soldering can find applications in repair of spacecraft such as satellites, space stations and interplanetary transport vehicles.

One technology that can be impacted by the inventive method is that of writable memory media such as compact discs (CDs) and digital video discs (DVDs). A writable CD or DVD, typically comprising an aluminum layer with a coating of translucent organic dye, is written by creating patterns of opaque features with a laser light at 780 or 650 nm, respectively. A rewritable CD or DVD typically uses a metal alloy instead of organic dye layer where a laser induced heating causes a phase change in metal alloy from crystalline to amorphous to create the light and dark digital pattern. A Blu-ray disc also employs phase change alloys for writing purposes using a 405 nm wavelength laser. Alternative disc technologies that can be used for writable memory media include fluorescent multilayer disc, 3D optical data storage, and polar high definition DVD. The common feature of all such technologies is the use of a laser for writing information by laser induced heating of a layer within the disc.

In one embodiment of the invention, a coating of functionalized fullerenes such as PHF on an organic dye or alloy layer of these disc memory devices can improve both writing speed and efficiency. In an embodiment for writable discs, the intensity of the laser can be higher than the threshold value for localized optical ignition of the fullerenes. In another embodiment for rewritable discs, the intensity of the laser can be attenuated to cause only localized heating of functionalized fullerenes without optical ignition.

In another embodiment coating of functionalized fullerenes can be employed as the sole layer for writing of digital information similar to protein coated discs. For reference, the size of the protein, bacteriorhodopsin, used in a protein coated disc, is around 3 nm allowing data storage greater than 1 Terabyte/inch$^2$. The size of functionalized fullerenes which can be decomposed during writing ("burning") is typically smaller than bacteriorhodopsin protein (about 1 nm versus about 3 nm), potentially allowing 9 times more information to be stored. The digital information can be read from the disc with techniques similar to those employed for protein-coated discs.

In an embodiment of the invention, the optical ignition property of functionalized fullerenes can be utilized for a spark-plug-like application. An example of a device is described as follows. Functionalized fullerenes such as polyhydroxy fullerenes (PHF) can be packed in a small tube with one end having small orifice and a means to deliver fullerene comprising molecules to the orifice in contact with a combustion chamber. A laser source (e.g., LED laser) of any wavelength is located nearby with the laser beam pointed towards the orifice. To start ignition the laser is turned on so that the laser beam illuminates the PHF particles present at the end of the tube. The laser irradiation can be in the form of a high intensity short pulse. Optical ignition at the end of the tube initiates combustion of the fuel-oxidizer mixture in a combustion chamber in a manner analogous to that of a spark plug in an internal combustion engine cylinder. The other end of the tube can contain a means, for example a plunger or a screw system, which delivers the PHF particles towards the orifice. The length of the tube can be adjusted to vary the interval at which the tube must be replaced or refilled with PHF. One of the major advantages of such a device over conventional spark plugs is operating temperature insensitivity. Conventional spark plugs are known to be less effective at low temperatures. The proposed device with functionalized fullerenes will be fully operable at very low temperatures because the mechanism of ignition differs in a significant fashion from that of conventional spark plugs (optical ignition vs. high voltage spark).

In one embodiment of the invention functionalized fullerenes can be used as fuel additives to improve the combustion properties and efficiencies of fuels, increasing the energy density of liquid fuels without altering their volatility. Such functionalized fullerene fuel additives can enhance combustion of the fuel at extremely cold temperatures. In such a case, the fuel with added functionalized fullerenes need only be used to initiate and establish stable combustion, switching to fuel free of fullerenes once combustion stabilizes in the warm engine. Another application for the fuels with added functional fullerenes is for use with unmanned air vehicles (UAVs). Increasing the energy density of the fuel would give UAVs longer ranges or loiter times. Use of functionalized fullerenes that are soluble in the fuel matrix would enable the energy density to be substantially increased with minimal or no change in fuel volatility or other properties.

Regarding medical applications, the present invention allows the delivery of remotely controlled heat instantaneously to regions within a human or animal body where functionalized fullerenes can be placed. This can permit precise methods for nanosurgery and nanotherapy. For example, cancerous tissues and cells can be selectively destroyed by use of external electromagnetic fields and radiations that release intense energy from the functionalized fullerenes but otherwise are harmless to the body. The functionalized fullerenes can be placed within the body by a variety of means, for example, when chemically attached to nanoparticle or other nanoscale object, and readily moved through the body and can have specific groups to target and attach to cancer cells.

In one embodiment of the invention, functionalized fullerenes can be conjugated with targeting agents, for example fluorescent antibodies or dye/quantum dot doped silica particles functionalized with antibodies or aptamers, and exposed to hazardous bioparticulates such as bacteria, virus, and spores. For example, carboxy fullerenes along with fluorescent dye or quantum dots can be encapsulated in a silica matrix. The surface of the matrix can be conjugated with targeting agents such as aptamers and antibodies. These multifunctional particles can then be dispersed in air or water for detection of hazardous bioparticulates, such as anthrax spores. The targeting agent can be used for the binding of the multifunctional particles on the surfaces of the bioparticulates. Irradiation with a low intensity electromagnetic source at an excitation wavelength of a dye or quantum dot can permit detection of hazardous bioparticulates by localized, relatively intense emissions from excited dyes or quantum dots that are part of multifunctional particles aggregated on the hazardous bioparticulates. The intensity of the electromagnetic source can be increased to heat, often causing a photoacoustic wave or igniting the functionalized fullerenes and inactivate the bioparticles.

In one particular embodiment, hyperthermia, or photothermal ablation, is realized using near-infrared radiation (NIR). Alternately, other frequencies can be employed, including radio frequencies in one embodiment of the invention. PHF molecules can be internalized by cancer cells through site targeted delivery. The internalized PHF can be then irradiated with a NIR source, such as a NIR laser. Since NIR can penetrate tissue, the technique can be non-invasive. Irradiation above threshold energy will lead to heating of PHF, increasing the temperature or generating a photoacoustic wave inside cancer cells that is sufficient to kill them. Currently, magnetic and gold nanoparticles are the most promising candidates for hyperthermia. Both types of nanoparticles are usually coated with a biocompatible layer and conjugated with targeting molecules. Applied magnetic/electric field and near IR are used for initiating temperature rise in these nanoparticles. However, little attention has been given to the fate of these nanoparticles. These nanoparticles can circulate in the body after treatment for a long period of time depending on the rate and mechanism of clearance. In contrast, PHF molecules according to the invention can be decomposed by a radiation induced ignition used to generate hyperthermia, allowing them to be readily eliminated from the system. Any excess of PHF nanoparticles circulating in the body can be non-toxic since PHF has been reported to display therapeutic properties such as an antioxidant, possibly reducing stress on the non-targeted cells and tissues.

Lasers have many applications in surgery including Laser-Assisted in Situ Keratomileusis (LASIK), laser-tissue welding (LTW), laser-tissue soldering (LTS), laser resurfacing and use of laser scalpels for cutting tissues or tumors (photodynamic therapy). One major side-effect of lasers is overheating, and in some cases thermal damage, of nearby tissues. Gold nanoshells have been employed for LTW and LTS to improve deep tissue heating and reduce thermal damage to surrounding tissues. In one embodiment of the invention, optical heating or optical ignition properties of functionalized fullerenes can be exploited for surgery in place of gold nanoshells to reduce the intensity of laser needed for localized heating or cutting of tissue, thereby limiting or preventing damage to surrounding tissues. Functionalized fullerenes can be used directly for these laser assisted embodiments or can be encapsulated in inorganic matrices, such as silica or titanium dioxide, or organic matrices such as poly(lactic-co-glycolic acid (PLGA) or chitosan.

In another embodiment of the invention functionalized fullerenes can be used as an explosion initiator. PHF, for example, can be ignited using radiation in excess of an intensity threshold. Radiation induced ignition is preferred for initiation of explosions as it is immune to electrical effects and is chemically stable. Conventional explosives require intensity on the order of $GW/cm^2$ for radiation induced initiation of an explosion. In comparison PHF can initiate the equivalent explosion with intensities on the order of $kW/cm^2$, thus decreasing the size and energy requirement of the radiation source. A majority of conventional explosives have nitrogen in their molecular structure. Certain bonds of nitrogen (N—N, $NO_2$) are unstable, which imparts instability to their structure. This instability is harnessed for explosive action. PHF and other functionalized fullerenes according to an embodiment of the invention do not have nitrogen atoms in their structures and the ignition is hypothesized to be due to localization of heat inside the molecule. Oxygen present in the PHF molecule may help in decomposition.

The explosion initiated from a fullerene comprising molecule can take place on a nanoscale or microscale fashion where a solid material is ripped or otherwise fractured from a pressure wave when the thermal energy is dissipated by a photoacoustic effect. These "nanoexplosions" can occur with the generation of a tortuous surface emanating from the fullerene comprising molecule.

In another embodiment of the invention, the optical heating or ignition of functionalized fullerenes can be used to provide a thrust vector. The rate of thrust can be modulated according to the quantity of functionalized fullerenes that is irradiated. In this manner the optical heating or ignition property of functionalized fullerenes can be used with or without other propellant for micro-thruster and nano-thrusters in space for precise positioning and rotation of satellites or other space vehicles. The functionalized fullerenes can be used exclusively as igniter and propellant or used in combination with other propellants such as polyvinyl chloride, polyglycidyl azide or polyvinyl nitrate.

In another embodiment of the invention, because functionalized fullerenes can absorb radiation across all wavelengths and release the absorbed energy as heat, the radiation absorption property of functionalized fullerenes can be utilized for solar heating applications. Functionalized fullerenes can be applied as a coating on metal, for example copper, surfaces of solar heaters for increasing the efficiency.

EXAMPLES

It should be understood that the Examples described below are provided for illustrative purposes only and do not in any way define the scope of the invention.

Example 1

Functionalized fullerenes, such as polyhydroxy fullerenes (PHF) and carboxy fullerenes (CF) were found to ignite when exposed to radiation through a wide range of visible and NIR wavelengths above a threshold intensity. Ignition led to instantaneous decomposition in air. The ignition process for PHF was observed with laser radiation at three different wavelengths; 785 nm (Near Infrared), 540.5 nm (Green) and 488 nm (Blue). The radiation induced ignition experiment with carboxy fullerenes and N-ethyl-polyamino-C60 was conducted with a 785 nm Laser. In both cases, the threshold intensity for observed ignition was less than 1 kW/cm$^2$.

Example 2

Figure 2:
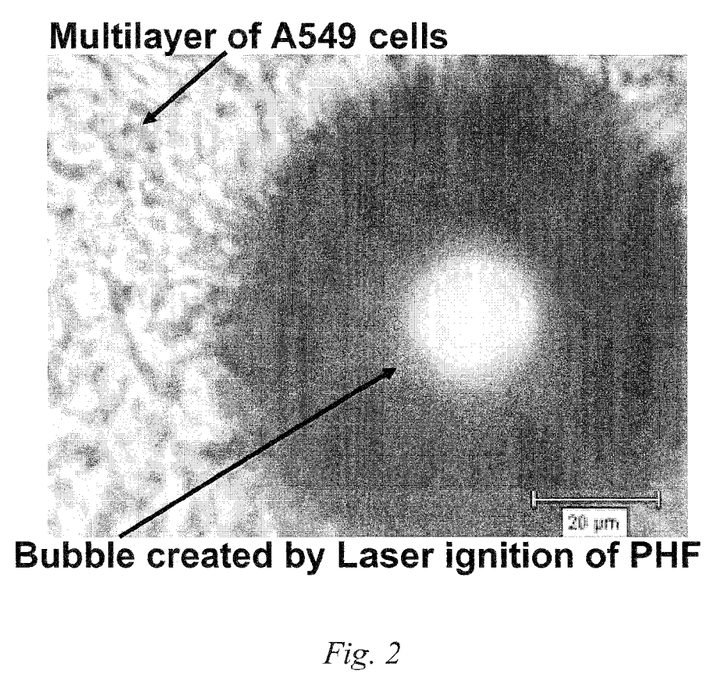
FIG. 2 shows an image of a bubble (resulting from localized heating) by laser ignition of Polyhydroxyl fullerenes (PHF) that were placed on top of lung mesothelial carcinoma cells (A549).

Experiments were conducted with A549 (Lung Mesothelial Carcinoma) cells. In a first step, varying quantities of PHF were placed on top of a multilayer of A549 cells cultured on magnesium fluoride crystals. The cells were submerged in aqueous growth media RPMI-1640, supplemented with 5% Fetal Bovine Serum and 1% Antibiotic, and exposed to a laser emitting at 785 nm wavelength. Sparking was observed at the focal point followed by popping sounds, which was attributed to either photo-acoustic effect or bursting of A549 cells. The observed damage to cells was dependent on the concentration of PHF. The damage was restricted to the top layer of cells at lower concentrations of PHF, whereas at higher concentrations of PHF, the ignition led to damage of multiple layers of cells as shown in FIG. 2, which shows a bubble created by laser ignition of PHF and clearly demonstrates the killing of the cancer cells.

Example 3

Figure 3:
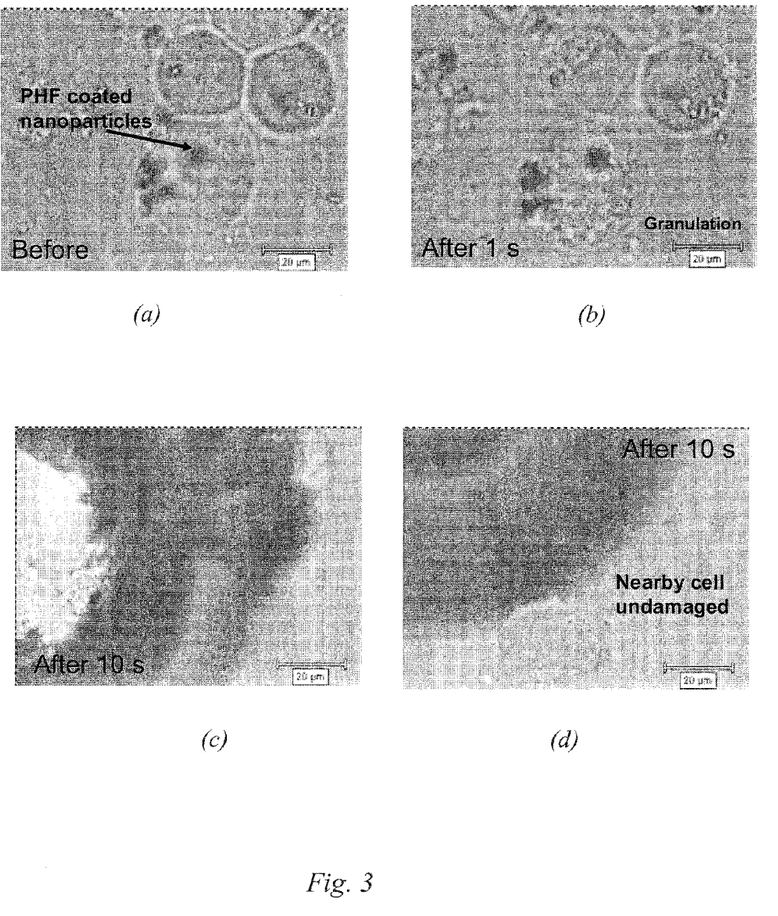

Another set of experiments was conducted with PHF coated on folate conjugated silica nanoparticles. The folate conjugation assists in uptake of nanoparticles by living cells, particularly cancer cells. The PHF coated nanoparticles were incubated for 24 hours with A549 cells in growth media for internalization. The A549 cells in the media were then exposed to radiation from a 785 nm laser for 1 second and 10 seconds as shown in the series of images presented in FIG. 3. After one second of exposure, the irradiated A549 cells appear granulated suggesting that the cells are under stress and in the process of cell death. This indicates that heating, short of ignition, of functionalized fullerenes causes granulation of associated cells. Further irradiation with the laser, for 10 seconds, resulted in radiation induced ignition and creation of a bubble. However, nearby cells were not affected, suggesting that hyperthermia can be controlled by focusing of the radiation.

Example 4

Figure 4:
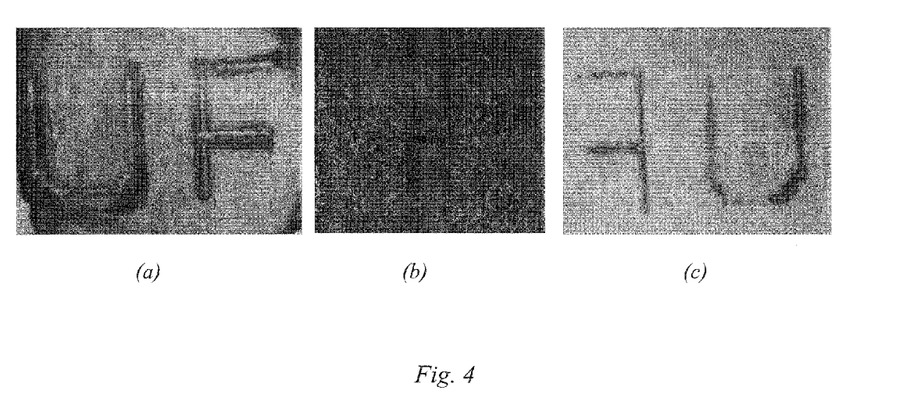
FIG. 4(a) is a photographic image of a front side view of PHF coated paper with "UF" inscribed using optical ignition of PHF according to the invention.
FIG. 4(b) is an image showing that the width of the inscribed line (50 μm) is close to the beam spot size of the laser used.
FIG. 4(c) is an image showing the back side of PHF coated paper with "UF" inscribed, showing that the paper was burned through to the back side by the optical ignition phenomenon.

Preliminary experiments were conducted with PHF coated paper. The coating was created by adding 50 microliters of PHF solution (1000 ppm in water) on paper which was subsequently dried. The coated paper was then exposed to laser radiation at 785 nm. The paper was manually moved to inscribe "UF" on paper. It is important to note that upon irradiation, the ignition of PHF and burning of paper was limited to the area of the laser spot. However, the heat generated was sufficient to burn the paper which evidences a temperature of >240° C. The degree of penetration of the inscription can be controlled with the concentration of PHF and intensity of irradiation. At higher concentrations of PHF or higher intensity of radiation, the "UF" pattern was burnt through the paper and could be observed on the backside of the paper as shown in FIG. 4(c).

Example 5

Fullerene comprising molecules were demonstrated to cause nanoexplosions in a nanocomposite of poly(methyl methacrylate) (PMMA) and polyhydroxy fullerenes (PHF) by an apparent photoacoustic wave emanating from the irradiated PHF. The PMMA-PHF nanocomposite displayed a dark brown color resulting from PHFs. Upon irradiating the PMMA-PHF nanocomposite with a 785 nm laser at about $10^2$ W/cm$^2$ a debris field formed after seconds of exposure, indicative of an explosion due to photoacoustic pressure or shock-wave.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A method of localized heating within an article, comprising the steps of:
    disposing a plurality of functionalized fullerenes selected from polyhydroxyl fullerenes, carboxy fullerenes, N-ethyl-polyamino-C60, [6,6] phenyl C60 butyric acid methyl ester (PCBM), fullerene hydride, N-methyl fulleropyrrolidine, or any combination thereof disposed in or on at least one target region comprising an organic gas, liquid or solid; an inorganic gas, liquid, or solid; a polymer or polymer composite; water, an aqueous solution or aqueous suspension; a nonaqueous solution or nonaqueous suspension; a metal or metal alloy; or a glass or ceramic; and
    irradiating said functionalized fullerenes with electromagnetic radiation to convert said radiation to thermal energy wherein said thermal energy dissipates as a photoacoustic wave emanating from said functionalized fullerene comprising molecule; and
    inducing a change in physical state or a chemical reaction in said target region by said photoacoustic wave wherein an article comprising said target region is altered.

2. The method of claim 1, wherein said electromagnetic radiation ranges from $10^{-12}$ m to $10^{12}$ m in wavelength and comprises gamma rays, x-rays, extreme ultraviolet, ultraviolet, visible, infrared, microwave, radio wave or any combination thereof.

3. The method of claim 1, wherein said chemical reaction is combustion.

4. The method of claim 1, wherein said article is a resist coating, wherein said chemical reaction is a chemical decomposition that forms negative features in said resist coating.

5. The method of claim 1, further comprising a step of etching, wherein said article is a resist coating, wherein said chemical reaction allows: selective etching of said target regions with a solvent to form negative features from the surface of the coating or channels within said coating; or selective etching of non-target regions with a solvent to form positive features from said target region.

6. The method of claim 1, wherein said target region comprises an interface in said article between a plurality of pieces of said article, wherein said change in physical state is melting and whereupon suspending said irradiation cools to form a weld between said pieces.

7. The method of claim 1, wherein said target region is a surface or portion of a solder comprising said organic solid, said inorganic solid, said metal, said metal alloy, said polymer or said polymer composite, and wherein said change in physical state upon said irradiating is melting, and wherein upon suspending said irradiation said solder cools and resolidifies.

8. The method of claim 1, wherein said target region comprises a layer of an inorganic dye, an organic dye, or a metal alloy within said article that is a writable memory medium, wherein said change in physical state or said chemical reaction changes optical properties of said layer in said target region.

9. The method of claim 1, wherein said target region comprises a layer within said article that is a writable memory medium, wherein said chemical reaction is decomposition that alters optical properties within said article.

10. The method of claim 1, further comprising the step of delivering said functionalized fullerenes from a reservoir to said target region, wherein said target region contacts a combustion chamber containing a fuel-oxidizer mixture and wherein said chemical reaction is ignition and combustion of said fuel oxidizer mixture.

11. The method of claim 1, further comprising wherein said article is a fuel-oxidizer mixture within a combustion chamber, wherein said functionalized fullerenes are dissolved or suspended in at least a portion of a fuel for said fuel-oxidizer mixture prior to introduction of said portion of said fuel to said article within said combustion chamber and wherein said chemical reaction is ignition and combustion of said article.

12. The method of claim 1, wherein said article comprises an explosive material, wherein said chemical reaction is an explosion.

13. The method of claim 1, wherein said article resident in a tube and wherein said chemical reaction is combustion to form combustion gases that are directed out of one end of said tube to provide a thrust, whereby said tube acts as a thruster.

14. The method of claim 1, wherein said change in physical state or chemical reaction forms a gas or a liquid with a division of said article at said target region.

* * * * *

UNITED STATES PATENT AND TRADEMARK OFFICE
CERTIFICATE OF CORRECTION

| | | |
|---|---|---|
| PATENT NO. | : 9,475,028 B2 | Page 1 of 1 |
| APPLICATION NO. | : 12/479300 | |
| DATED | : October 25, 2016 | |
| INVENTOR(S) | : Vijay Krishna, Brij M. Moudgil and Benjamin J. Koopman | |

It is certified that error appears in the above-identified patent and that said Letters Patent is hereby corrected as shown below:

In the Specification

Column 6,
Line 11, "can be farther" should read --can be further--.

In the Claims

Column 14,
Line 11, "said article resident" should read --said article is resident--.

Signed and Sealed this
Twenty-sixth Day of September, 2017

Joseph Matal
*Performing the Functions and Duties of the
Under Secretary of Commerce for Intellectual Property and
Director of the United States Patent and Trademark Office*